United States Patent [19]

Herschler

[11] Patent Number: 4,559,329

[45] Date of Patent: Dec. 17, 1985

[54] DIETARY AND PHARMACEUTICAL USES OF METHYL-SULFONYLMETHANE AND COMPOSITIONS COMPRISING IT

[76] Inventor: Robert J. Herschler, 3080 NW. 8th Ave., Camas, Wash. 98607

[21] Appl. No.: 601,771

[22] PCT Filed: Sep. 13, 1983

[86] PCT No.: PCT/US83/01396

§ 371 Date: Apr. 17, 1984

§ 102(e) Date: Apr. 17, 1984

Related U.S. Application Data

[60] Continuation-in-part of Ser. No. 418,110, Sep. 14, 1982, and a continuation-in-part of Ser. No. 277,592, Jun. 26, 1981, Pat. No. 4,477,469, which is a division of Ser. No. 71,068, Aug. 30, 1979, Pat. No. 4,296,130.

[51] Int. Cl.$^4$ ............ A61K 31/42; A61K 31/43; A61K 31/44; A61K 31/135; A61K 31/605; A61K 31/10; A61K 31/19; A61K 31/34; A61K 31/40

[52] U.S. Cl. ............................ 514/164; 514/199; 514/357; 514/372; 514/420; 514/474; 514/557; 514/652; 514/708

[58] Field of Search ............... 424/337, 230; 514/164, 514/199, 357, 372, 420, 474, 557, 652, 708

*Primary Examiner*—Stanley J. Friedman
*Attorney, Agent, or Firm*—Millen & White

[57] ABSTRACT

Methylsulfonylmethane ($CH_3SO_2CH_3$) administered orally is effective in ameliorating the symptoms of gastrointestinal upset, e.g., produced by the ingestion of aspirin and other pharmaceuticals, and of allergic reactions. Oral compositions containing a mixture of such a pharmaceutical and methylsulfonylmethane are useful in avoiding the gastrointestinal upset which otherwise occurs when ingesting the former.

11 Claims, No Drawings

DIETARY AND PHARMACEUTICAL USES OF METHYL-SULFONYLMETHANE AND COMPOSITIONS COMPRISING IT

This is a continuation-in-part of U.S. application Ser. No. 418,110, filed Sept. 14, 1982, and Ser. No. 277,592, filed June 26, 1981 U.S. Pat. No. 4,477,469 which is a division of Ser. No. 071,068, filed Aug. 30, 1979, now U.S. Pat. No. 4,296,130.

BACKGROUND OF THE INVENTION

This invention relates to methods for the use of methylsulfonylmethane (MSM) to normalize body functions in subjects displaying symptoms of physiological response to stress, specifically gastrointestinal upset, inflammation of the mucous membranes and allergic reactions and to pharmaceutical compositions for use therein.

In my prior U.S. Pat. No. 4,296,130, I disclose compositions containing MSM to soften, smooth, lubricate and preserve the pliancy of human tissue, for reducing the brittleness of finger and toe nails. I disclose therein that MSM is a naturally occurring substance found in the tissue and body fluids of higher animals. I disclose in that patent that MSM is substantially inert to the chemistry of the body and, because of its extremely low toxicity and inertness to the diverse chemical reactions involved in the processes of life, it can be used as a diluent for blood. The ingestion of oral compositions is disclosed therein to preserve the pliancy of intestinal and other tissue.

U.S. Pat. No. 4,296,104 discloses DMSO compositions which optionally can contain a protein modifying agent, such as MSM. U.S. Pat. No. 4,112,946 discloses the use of an aqueous solvent system comprising MSM in a process for the introduction of a health modifying agent into water-living animals as an osmotic factor.

J. J. Kocsis et al., Annals N.Y. Acad. Sci. 243, 104–109, (1975), cite literature which report that MSM, a known metabolite of dimethylsulfoxide, persists for as long as three weeks after percutaneous application in man and one week after i.v. administration. The authors report that MSM, like DMSO, enhances urinary taurine secretion produced by aromatic hydrocarbons in man; antagonizes the lethal effects of anticholinesterases such as paraoxon, tetraethyl pyrophosphate and octamethyl pyrophosphoramide; lowers the body temperature of rats exposed to 5° C. temperature; and reduces motor activity (when administered i.p.). Kulshestha et al., C.A. 83; 22910n (1975) report that MSM inhibits *L. citrovorum* at 10 ppm except early in incubation. MSM occurs naturally in a variety of fruits, vegetables and vegetable products, grains in at least trace amounts ($\leq 3.3$ ppm). T. W. Pearson et al., C.A. 95:113654w (1981). It is present in small amounts in normal urine. Williams et al., Archs. Biochem. Biophys. 1966, 113, 251–252. The following Chemical Abstracts refer to the biological aspects of MSM: as DMSO metabolite, in cattle, 83:183a; *Escherichia coli* inhibition by, 83:72577e; nervous system depression by, 84:173608a; *Salmonella typhimurium* inhibition by, 82:71; of urine, as DMSO metabolite, 77:96734f; alk. phosphatase activity of, 67:115529e; antimicrobial activity of, 73:63515h; enzymes of liver in response to, 75:108136m; of urine, 75:86025v; heart response to, 74:2429y; lung constrictivity activity of, 62:9634f; in tissue culture protection against X-rays, 58:9391e; toxicity of, 63:8915b; toxicity of, ETOH and, 64:7229h; in urine after administration of, 65:17537g; in urine of humans, 64:10170g; and in urine as DMSO metabolite, 64:7213a; 65:17535b.

I have now found that notwithstanding the fact that MSM is omnipotent in body fluids and is so non-toxic that it can be used as a diluent for blood without upsetting the blood chemistry, MSM is an ameliorating agent for a variety of pathological conditions when administered systemically and preferably orally to persons displaying symptoms of physiological response to stress, e.g., gastrointestinal distress, inflammation of the mucous membranes and allergic reactions.

In particular, I have found that when those stress response symptoms include gastrointestinal upset, e.g., diarrhea, constipation, nausea, hyperacidity and/or epigastric pain, or inflammation of the mucous membrane, especially of the gastrointestinal and/or respiratory tract, dramatic relief from those symptoms can be achieved by the oral ingestion of MSM.

I have also found that the oral ingestion of MSM can be beneficial in treating a variety of other conditions that one would not expect to be responsive to MSM.

Accordingly, it is an object of this invention to provide a method for the amelioration of physiological symptoms of stress employing MSM.

Another object is the provision of pharmaceutical compositions comprising a stress-inducing physiologically acceptable pharmaceutically active agent and a stress-relieving amount of MSM.

Other objects will be apparent to those skilled in the art to which this invention pertains.

SUMMARY OF THE INVENTION

In a method of use aspect, this invention relates to a method for normalizing body functions of a patient displaying symptoms of physiological response to stress which comprises orally administering to the patient an amount of MSM effective to ameliorate those symptoms, especially to patients manifesting at least one of gastrointestinal upset and inflammation of the mucous membrane.

In another method of use aspect, this invention comprises administering to a patient manifesting symptoms of an allergic response, an amount of MSM effective to ameliorate those symptoms.

In a composition aspect, this invention relates to pharmaceutical compositions comprising an admixture of a stress-inducing but otherwise physiologically acceptable pharmaceutically active agent, e.g., one whose side effects includes gastrointestinal upset in persons ingesting that agent, and a stress-relieving amount of MSM, e.g., an amount effective to ameliorate the gastrointestinal upset.

DETAILED DISCUSSION

A single oral dose of MSM is usually not effective to ameliorate the aforesaid symptoms. Therefore, the MSM is usually administered in successive spaced dosages, either periodically throughout the day or on successive days, or both, until such amelioration occurs, e.g., for 2 to 21 days or even longer. The amount of MSM in each dose usually is not critical, particularly when several successive doses are administered, because the ingested MSM accumulates in the body tissues and fluids, i.e., reaches an effective titre. Individual doses of as low as 50 mg. are sometimes effective and doses as high as 1,500 mg. or more are well tolerated. The usual individual dose is about 100–1,000 mg., preferably 250–500 mg. Total daily dosages of 100–5,000 mg., preferably 250–2,000 mg., more preferably 500–1,500 mg., are usually employed. The effective dosage depends to some extent on the nature and severity of symptoms manifested; the cause of those symptoms; and the MSM blood level of the patient prior to the administration of the MSM thereto. It appears that healthy persons may have MSM blood levels of at least 1 ppm and patients displaying the aforesaid symptoms often have depressed MSM blood levels. Desirably, enough MSM is administered to raise blood levels to above 0.5 ppm and preferably at least 1 ppm, e.g., to as high as 10–20 ppm. However, blood sampling for MSM content ordinarily is not required because the oral ingestion of amounts of MSM in excess of that required to elevate MSM blood levels is not harmful because of the non-toxic nature of MSM.

The MSM can be administered orally in any convenient manner, e.g., by ingesting the crystalline MSM or an aqueous solution thereof. Preferably, the MSM is administered in unit dosage form, e.g., as a tablet, capsule, dragee or pill, as such or in admixture with the usual pharmaceutically acceptable excipients, diluents, tableting aids, etc. Tablets and capsules are preferred, especially those containing from 100 mg. to 500 mg. MSM each.

Although human beings are the preferred patients, other mammals, e.g., domestic animals such as horses, cows, sheep and pigs, pets, e.g., cats and dogs, and wild animals kept in zoos, can be treated according to this invention. Both small children and adults, including geriatric patients, can be successfully treated.

Because MSM is naturally present in the body fluids and tissues of most if not all normal mammals, its mechanism of treating the physiological symptoms of stress appear to be less than that of a drug and more like a dietary supplement, such as is achieved with large dosages of vitamins. Although MSM has not yet been established to be a vitamin, at least a vitamin deficiency-type disease has not yet been shown to occur in patients with abnormally low MSM blood levels, it does have a vitamin-like moderating or normalizing activity for various body functions, as there appears to be a high correlation between abnormal physiological symptoms and low MSM blood levels in human beings. Whether this is due to the inability of such individuals to adequately store MSM from natural sources thereof, to inadequate amounts of MSM in the diet of those individuals or to the depletion of the MSM usually present in the body as a result of the abnormal condition, is not known. Whatever the reason, the oral ingestion of MSM in sufficient amounts will ultimately bring MSM levels to or above those usually present in healthy mammals and will ameliorate a variety of symptoms associated with stress.

Like vitamin C, glucose and other substances normally present in vertebrate diets, MSM exhibits remarkably low acute and chronic toxicity in the hosts diet. Primates with high MSM blood levels for up to two years lack evidence of MSM toxicity.

Although MSM is found as a natural constituent of foodstuffs, like vitamin D the principal supply in vertebrates is believed to be synthesized by the body using dimethyl sulfide or one of its naturally occurring precursor salts as commonly found in meat, fish, vegetables and fruit. Too low a body concentration of MSM results in adverse physical and psychological stress, tissue and organ malfunction, fatigue and increased susceptibility to diseases.

Based on the excretion rate from young compared with older animals, MSM appears to be found in lowering concentrations with increasing age. Generally there is less than 0.5 ppm in the humoral fluid. In the blood of adult man, the level of MSM detected by gas chromatography techniques can be less than 0.25 ppm. This may explain why MSM has proved generally more useful as a dietary supplement with adults, in whom naturally occurring levels of MSM, as in other vertebrates, generally are lower than optimum for providing optimum protection of the organism from stress challenge, because a conventional balanced diet cannot supply the minimum requirement for optimum health. For example, milk, one natural source of MSM, contains only about 2–5 ppm depending on the source. To obtain and retain a miminum blood level of MSM of about 1 ppm, a subject would be required to ingest an impractically large amount of this or any other natural food product. According to this invention, the diet of man and lower animals is supplemented with sufficient MSM, preferably daily, to at least maintain a body concentration of 1 ppm and, where health is threatened, a level of 10–20 ppm or higher.

Although this invention is directed primarily to MSM-containing pharmaceutical compositions adapted for oral ingestion, MSM has been demonstrated to be useful in other oral forms, e.g., mouth washes and toothpaste preparations, because of MSM's chemical and light stability, low toxicity, good solvency, water solubility and dispersibility.

MSM, alone or in combination with an appropriate pharmaceutically active agent, has demonstrated usefulness when introduced into other body cavities, e.g., vaginally and rectally. MSM can be introduced into the lungs and bronchial tree as an aerosol of a solution thereof or as a sublimate produced by heating, which can be inhaled.

Surprisingly, parenteral injection does not appear to be as effective as other routes of administration.

MSM given at tolerated levels by intraperitoneal injection to mice infected with Plasmodium berghei did not alter the infection in any measurable manner. As a follow-up experiment, white rats were given 10 mg/100 g. body wt. i.p. and blood levels determined 1-hour post. MSM blood level was negligible (less than 0.25 ppm—blood level), suggesting that i.p. administered MSM is not absorbed, at least not readily. This experiment suggests that i.p. administration of MSM is not a viable alternative, and again illustrates that minimum blood levels of 1 ppm are required if the body is to overcome an undesirable hazard.

The sources of stress which result in a physiological response thereto which comprise one or more of gastrointestinal upset, inflammation of the mucous membrane and allergic reactions, are highly diverse. Although MSM may not necessarily eliminate the underlying physiological condition which provokes these symptoms, by ameliorating the symptoms permits more rapid return to normalcy. Examples of sources of stress which provoke such a physiological response thereto are parasitical, microbial and fungal infections, ingested pharmaceutical drugs, e.g., aspirin and other analgesics, antibiotics, and numerous other drugs whose gastrointestinal side effects include one or more of nausea, diarrhea, constipation, indigestion, hyperacidity, gastric pain and flatulence; inflammation of the lungs, e.g., from smoking, respiratory infection, chronic lung ailments or allergies; allergic reactions, e.g., respiratory congestion, skin rash, hives and gastrointestinal upset, to food, drugs and environmental materials, e.g., house dust, pollen, wool, animal hair, feathers and other diverse allergens, and insect bites.

Allergy is an abnormal tissue reaction to allergen challenge in both man and lower animals. It is a particular problem in man with recognized allergic problems affecting about 15% of the world's population. A much larger percentage experience low level allergy, i.e., below that considered debilitating, yet reductive of optimum health. The environment of primitive man contained many allergens causing abnormal tissue responses. Today's population exposed to a more hazardous environment is targeted with many more allergen challenges. MSM has a broad and profound beneficial effect in ameliorating diverse allergic responses.

MSM, taken at levels of about 50-1,000 mg/day in the diet ameliorates allergic reaction to inhalant, ingestant, contact and infectant allergens. MSM has been shown to be a favorable normalizing moderator of injected allergens as well. Subjects find a direct correlation between systemic concentration of MSM and resistance to allergens.

MSM does not necessarily totally eliminate the allergic response against allergens. However, in such cases, the degree of relief can be enhanced by conventional anti-allergy medication, whose effect is ordinarily manifested at lower levels of administration when taken with MSM than when administered alone.

MSM can be administered in any convenient form adapted for oral ingestion, for example, solid unit dosage form, e.g., tablets, capsules, dragees and pills; as a liquid solution, e.g., elixirs and syrups, or in particulate solid form, e.g., granules, crystals or powders. Since MSM has an additive flavor or flavor enhancing property, e.g., for chocolate, soy sauce, salt, sweet vermouth and other alcoholic beverages, carbonated cola beverages, rye bread and other baked goods, it can be included in condiments and admixed or co-crystallized with NaCl or other particulate flavorings and condiments. MSM can also be safely administered by intravenous or parenteral injection. Additional benefits are seen when MSM is provided in combination with the water-soluble vitamins.

In one embodiment of this invention, the MSM is provided as a mixture of a gastrointestinal upset-promoting physiologically acceptable pharmaceutically active agent and a gastrointestinal upset-ameliorating effective amount of methylsulfonylmethane. Such mixtures are preferably adapted for oral ingestion, e.g., tablets, capsules, dragees or pills, and preferably contain about 100 to 1,000 mg. MSM, more preferably from 250 to 500 mg., per solid or fluid unit dosage. The gastrointestinal upset-inducing agent is preferably an analgesic, e.g., aspirin. For a listing of pharmaceutical drugs whose side effects include gastrointestinal upset, e.g., nausea, diarrhea, constipation, hyperacidity, and/or flatulence, see the 1982 Edition of the Physician's Desk Reference, whose disclosure is incorporated herein by reference.

In addition to aspirin and other analgesics, specific examples of other drug classes whose gastrointestinal side-effects are ameliorated by the concurrent ingestion of MSM are antineoplastics, antiinflammatories, cardiovascular, antibiotics and other chemotheropentants for microbial diseases.

As stated above, MSM also manifests beneficial effects in other diverse situations where such an effect would not be expected. The following are illustrations of such beneficial effects.

Oral Hygiene: Subjects not having professional dental cleaning for at least four-six months and demonstrating minor yet discernable gum inflammation, probably due to plaque irritation, were given either a paste or powder prepared by combining commercial dental products with MSM on a 50/50 w/w basis. Subjects used one or the other to cleanse their teeth on twice daily regimen. Following one week use, the oral mucosa was free of signs of inflammation. One subject (T.K. M 22) troubled with recurring canker sores reported freedom from this problem during and after the one month testing was terminated. MSM, a solvent and dispersant in aqueous media, was shown to be an excellent agent alone or as an additive in combinations for the cleansing of teeth and the buccal cavity.

Bad breath associated with smoking or food, such as onion and garlic, is reduced or eliminated by cleansing the teeth and mouth with an MSM-containing preparation. Subjects of this test with a viscid mucoid nasopharyngeal discharge experience a reduction in the viscosity of the mucous and generally a productive cough. Interestingly, two subjects with a restricted sense of smell found a sharpening of this sense while MSM was being evaluated by them in a gargle. Critical observers noted their sense of taste was improved.

Maintenance of Good Health: 14 subjects of both sexes, all in apparent good health, ages 33-59, were given oral MSM in amounts ranging from 250 to 500 mg. daily which maintained blood level above 1 ppm. These individuals were continued on MSM, taken as a solution in orange juice for periods of from about seven months to over one year. None of the 14 became ill during this testing and each reported feeling better and stronger with increased endurance while MSM was a part of their diet.

Connective Tissue and Dermatologic Disorders: Primary and secondary pruritis, acne (including Grade 4), acne rosacea and diverse other dermatological problems which are often allergy related respond favorably to a diet supplemented with MSM. Pruritis due to various causes and acne respond promptly to diet supplemented levels of about 100-1,000 mg. per day. Teenagers found MSM in cola drinks a particularly acceptable satisfactory combination when treating acne. With rosacea, visual improvement was much slower. In one subject (J.H., F 51) daily ingestion of 500 mg. MSM for at least several weeks was required before telangiectasis dimished.

Inflammation of the Eye: A 15% solution of MSM in isotonic saline was evaluated and found to be a soothing treatment for the eye following accidental injury due to particulate matter in the eye as dust or pollen. A rabbit eye, irritated with aqueous sodium lauryl sulfate, quickly cleared when treated every hour with a 10% aqueous solution of MSM.

Pain Associated With Systemic Inflammatory Disorders: Individuals presenting signs and symptoms of pain and inflammation associated with various musculoskeletal system disorders reported substantial and long lasting relief while including from about 100 up to about 5,000 mg. of MSM per day in their daily diet. Most, trying first MSM alone, then a combination with ascorbic acid, reported greater benefit with the combination. The combination of MSM with ascorbic acid was seen to be particularly useful in correcting night leg cramps. Migrane suffers have obtained substantial relief at oral doses levels of 50–500 mg/day.

As a specific example, one subject (M.P., F 81) presented chronic arthritis with painful involvement of the lower trunk. Over the years she had evaluated most new antiarthritic, analgesic drugs with disappointing results. She included MSM at ½ tsp. daily in her diet and found almost total pain relief by the end of the second week. After ingesting MSM daily at ¼–½ tsp. for about 16 months, the subject is enjoying a substantially pain-free life.

Mental Normalcy: In man mental normalcy is demonstrated by alertness with an inner calmness which is not subject to sharp swings in mood change. Individuals on MSM generally report increased alertness, a plateau of mood changes, and particularly very infrequent depression. A few subjects on medication intermittently for depression observed that MSM relieved depression within hours rather than days, as had been their prior experience with antidepression medication. Students report that while taking MSM, their ability to concentrate is enhanced. MSM therefore is useful in conjunction with CNS therapeutants. The most useful application for MSM seen to date in the field of mental normalizing is as an aid to the terminally ill, to relieve anxiety and depression.

Wound Healing: Four sets of 5 hamsters were subject to scarification of the right cheek pouch using standard methodology. One week prior to pouch injury, one set was started on a daily regimen of 0.1 gm/kg of MSM in the diet, a second group was given 0.1 gm/kg of MSM plus 100 mg. of ascorbic acid, a third group was given only 100 mg. of ascorbic acid, while the last group, fed on a standard hamster feed was held as control. Daily post-scarification examination was made to determine the rate of injury repair. At 36 hours, the animals receiving MSM plus vitamin C orally had sharply reduced inflammation about the wounds and prominent healing granulation. This baseline result was matched by day three with both MSM alone and vitamin C alone treated subjects. By day 4 and 5, controls (no medication) matched the healing status seen at 36 hours with those animals receiving the MSM/vitamin C combination.

Diet Supplement in Animals: Young laboratory animals, including dogs, consistently increased weight at a greater rate over controls where MSM was included in their water and/or food. This was observed at both low and high dosage levels. An explanation for this is that any minor allergic response from the diet was neutralized by including MSM therein. Additionally, the fur quality improved and somewhat faster nail growth was noted. Weight increases were not seen with adult animals during feeding experiments.

Parasite Infection (Enterobius): Laboratory mice determined by fecal cast examination to have pin worms were given 2% by wt. MSM in both their commercial feed and drinking water, ad lib. Examination 17 days after test initiation indicated the fecal cast were free of worms and eggs. The blood level of MSM in the one animal examined exceeded 30 ppm.

These examples of MSM's ability in returning parasite susceptible tissue to normalcy where host injury is minimal or nil, illustrates that MSM in the diet aids in overcoming varied microbial infections, not by attack on the organism, but by strengthening body resistance thereto.

MSM antagonizes anticholinesterases in vivo and possesses weak in vitro antibacterial action, for example, against *Escherichia coli, Leuconostoc citrovorum, Salmonella typhimurium, Staphlococcus aureus* and *Streptococcus thermophilus.*

An evaluation of MSM as concurrent therapy with conventional anti-malaria drugs is indicated. Around one million humans die annually from this parasitic infection. Testing to date indicates that MSM is a useful adjunct with the therapeutic modalities used to combat adverse health problems by increasing a subject's baseline reistance to adversity and moderating untoward effects associated with drugs, vaccines and physical assaults against illnesses as by radiation or hyperthermia.

Vascular Complications Associated With Diabetes: A subject (F.B., M 58), diagnosed to have diabetes mellitus 22 years earlier was seen with a serious vascular complication. Arteriosclerosis had decreased the arterial blood supply to the lower limbs resulting in chronically cold feet and intermittent claudication. In addition, the subject had suffered a bruise to the foot which was not healing. This subject received 500 mg. of MSM with 250 mg. of ascorbic acid twice daily over a period of 21 days. The first observed improvement was the healing rate of the bruise. By the end of the third week, the cold foot problem was partially relieved and the subject was able to double his walking distance without undo tiring. Post treatment laboratory workup suggested a possibility that his insulin requirement could be reduced.

From the foregoing and the examples hereinafter, it can be seen that MSM is useful inter alia in the treatment of gastrointestinal upset, moderation of allergic responses, control of gut and urogenital infections, improving lung function, improving oral hygiene, for the treatment of pain syndrom, insect bites, wheal and flare moderation, hypertension, treatment of depression, acne and as a growth stimulant for animals and as a food flavor enhancer.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

Acute Pain: MSM administered orally has proven useful in relieving acute pain in the mid-back region of an adult male caused by calculi obstructed ureter with a single 1.5 gm dose dissolved in warm water, and pain spasms in the lower abdomen region of an adult female resulting from an accidental blow to the abdomen (two 1 gm. doses in warm water at 4 hour intervals).

Low Platelet Count: MSM administered orally raised the platelet count of an adult female with lupus erythematosus from 84,000 (after prednisone therapy) to 200,000 over a two year period (1.5 gm/day in 3 doses).

Sun and Wind Burn: Persons ingesting from 0.5–2 gm/day of MSM suffered only mildly from about 4 hours exposure to summer sun and wind, whereas their companions were severely sun and wind burned.

Pleuritis: Bilateral fibrinous pleuritis developed in a breeding mare with a respiratory infection, which did not respond to six weeks of conventional antibiotic and anti-inflammatory therapy, responded favorably (normal breathing, negative ausculation of the chest) after five days of MSM (2×12 gm/day in diet).

Post-Athletic Activity Fatigue: The physical fatigue syndrome following intense athletic activity in competitive sports which usually persists for 8-10 days in athletes was gone in 2-3 days in individuals who had ingested MSM (from 1-2 gm/day in split dosages) for the preceding six months.

Tableting and Granulation Aid: Pharmaceutical compositions adapted for oral ingestion in the form of tablets, granules or free flowing powders and comprising a pharmaceutically active agent in admixture with an adjuvant, viz., a tableting aid, a granulating aid or a flow promoting agent, respectively, have improved properties when the adjuvant consists predominantly, essentially or totally of MSM. Time-release and release-rate modification of the pharmaceutically active agent from the composition to the patient can be achieved by its dispersion or dissolution in an MSM matrix. Other dilutents and binders, when the composition is in filled capsule or tablet dosage form, which can be used in combination with the MSM are colloidal or fumed silica, calcium carbonate and calcium mono-, di- and triphosphate.

MSM can be used as a dry granulation aid by forming a melt thereof with the pharmaceutically active agent uniformly dispersed or preferably dissolved therein; solidifying the melt; and breaking the resulted solid into granules, which can then be screened, or further reduced into a free flowing powder which can readily be compressed into tablets with superior physical properties, compared to those employing conventional tableting aids, especially when combined with 0.25 to 2% colloidal silica.

MSM is particularly useful as a granulation and tableting aid for pharmaceutically active agents which are unstable in the presence of moisture, i.e., which loose a portion or all of their activity upon storage in the presence of the 2% or more moisture required by conventional granulation and tableting aids in order to be operable. Therefore in a preferred embodiment, this invention relates to substantially anhydrous, i.e. less than 1% by weight moisture content, mixtures of MSM and one or more pharmaceutically active agents which are storage unstable in the prsence of moisture, e.g., vitamins, biological extracts, antibiotics, etc., preferably in the form of a free flowing powder, granules or tablets, dragees or pills.

In each example, the subject is a human being, unless stated otherwise. Their initials, sex and age are in parenthesis.

GASTROINTESTINAL UPSET

EXAMPLE I

Diarrhea Associated With Parasite Gastrointestinal Infection

*Giardia lamblia* is a microorganism believed to be responsible for some cases of "traveller's diarrhea," particularly persistent diarrhea which is refractory to antimicrobial therapy. Like many intestinal parasites, the resistance to the organism varies from individual to individual and therefore in part is an immunological problem. MSM appears to augment immunological competence which explains, at least in part, why MSM is effective in treating infections of this parasite. In in vitro testing, concentrations of 1 mg/ml and lower, MSM demonstrated no significant inhibition of Giardia but was strongly inhibitory at 20 mg/ml concentration. Concentrations above 40 mg/ml provided prompt kills of the microorganism.

One subject (M.H., F 44) with confirmed Giardia, apparently contacted from contaminated water in a primitive area, given 500 mg MSM three times daily for 14 days, was asymptomatic by the eighth day. Two stool specimens collected one week apart were free of the microorganism.

Since Giardia and other organisms are suspect with "traveller's diarrhea," and the stress of vacations in foreign countries can upset GI tract normalcy, MSM solution was combined with bismuth subsalicylate (Pepto-Bismol ®) at a level that would provide about 300 mg of MSM per ingested tablespoon of the combination. Four of seven couples travelling together to a central American country were given the above combination and the other three carried unmodified bismuth product. Each of the couples were instructed to take one tablespoon of their version of the bismuth product each morning and evening during each of the 8 days of the trip. None of the couples taking the bismuth product containing MSM experienced stomach upset, nausea or diarrhea during the trip and after returning home. Four of the six taking only the unmodified bismuth product experienced some degree of GI tract disturbance, one experiencing severe diarrhea. The minimum blood levels of the subjects ingesting the MSM during this testing would 10 ppm. One of the individuals (M.M., F 34), taking the MSM-Pepto bismuth ® combination had a history of GI upset with travel seemingly triggered by uncontaminated but new sources of food and water of differing composition, which is consistent with MSM's ability to relieve the GI tract stress imposed by noneffective challenges.

EXAMPLE II

Aspirin Gastrointestinal Upset

A subject (G.S., F 54) with a 12-year history of rheumatoid arthritis primarily involving the hands obtained pain relief with aspirin but was hypersensitive to the drug, which produced severe gastric upset, even with infrequent use.

In order to obtain a current sensitivity threshold determination, the subject ingested two 5 grain aspirin with water and within a span of 15-20 minutes complained of gastric pain, nervousness and nausea. The following day, the subject ingested two buffered aspirin tablets (Bufferin ®) each containing 7.5 grains of aspirin. The subject again experienced a hypersensitivity reaction, judged as severe. On the fourth day, the subject ingested two capsules each containing a mixture of a pulverized 5 grain aspirin tablet and 500 mg. of MSM. Within the first 0.5 hour, the subject experienced a feeling described as "queasy" but experienced neither stomach pain nor nausea. Following this favorable response, the subject ingested two capsules containing 325 mg aspirin and 500 mg of MSM three times daily for two weeks without discomfort and experienced relief of hand joint pain.

Following this initial testing, two subject (J.K., F 54; T.H., F 57) with a history of aspirin intolerance, and both with a diagnosis of chronic arthritis, were provided capsules containing a mixture of 250 mg aspirin and 350 mg MSM, taking two capsules T.I.D. for a period of two weeks. Both subjects tolerated the MSM-formulated aspirin without adverse effect and experienced pain relief.

EXAMPLE III

Gastrointestinal Upset From Non-Steroid Anti-Arthritic Drugs

A. A subject (R.S., M 54) with arthritis had been evaluated with Naprosyn ®, a non-steroid analgesic and found to be intolerant of the drug at a dosage of 250 mg taken twice daily. The subject complained of unacceptable gastrointestinal upset and headache. The above dosage of Naprosyn ® was re-evaluated in this subject giving a 500 mg capsult of MSM concurrently with the 250 mg tablets of Naprosyn ®. When administered with MSM, the subject experienced no side effects and obtained pain relief.

B. Two subjects (C.W., F 27, J.R., M 66) with gastrointestinal intolerance for Indocin ®, a non-steroid anti-arthritic, when taken at dosages above 25 mg with food twice daily, were evaluated with concurrently administered 250 mg units of MSM dissolved in water. Both tolerated first 50 mg dosages B.I.D., then 75 mg dosages B.I.D., taken over a three week period, without adverse effect except mild drowsiness seen in one, perhaps not drug related. The tolerated medication level provided symptomatic relief of their arthritis.

C. One subject (C.H., M 47) responsive to Motrin ®, a non-steroid anti-arthritic drug, developed a hypersensitivity thereto, as evidenced by epigastric pain with nausea. This subject was given 500 mg of MSM dissolved in milk three times daily and one 300 mg tablet of Motrin ® taken from 5–15 minutes following ingestion of the MSM. With MSM as a companion part of the regimen, Motrin ® tolerated without side effects.

EXAMPLE IV

Hyperacidity

At least 75% of those individuals taking one or several of the plethora of antiacid/antiulcer medications, such as metal hydroxides or histamine H-2 receptor antagonists, can sharply reduce or eliminate such potentially harmful medication within a week of initiating MSM as a dietary supplement. The most common level of ingestion of MSM has been 500 mg/day taken in the morning or as a twice daily split dose. One subject (J.J., M 44), a user of antiacids on a daily basis of years, obtained complete relief by taking 5 mg of MSM, three times daily in capsule form in combination with sucrose as a diluent of the capsule fill. Ingestion of antiacids, cimetidine HCl, etc., while countering one problem often sometimes creates serious other untoward effects. Since MSM often is more effective than even combinations of H-2 receptor antagonists and neutralizing antiacids, this suggests that gastric acid secretion and digestive enzyme release is more complicated than has been believed. The response to even low levels of MSM suggests that man's renal threshold for MSM varies sidely from individual to individual.

EXAMPLE V

Irregular Bowel Movements

During the evaluation of the patients described hereinafter with lung disfunction, two seemingly opposite, but normalizing actions of MSM were recorded. A subject (B.K., F 63) with a long history of constipation obtained relief of this problem while ingesting at least 250 mg/day of MSM. In seeming contrast, another male subject (H.B., M 48) had suffered with moderate to severe diarrhea, possibly due to his cancerous condition and medications. The problem of diarrhea cleared up by the third day after MSM was included in his diet at a level of about 750 mg/day.

These MSM responses by an over- and underactive colon were further studied. Twenty-one subjects with a history of constipation and three with chronic diarrhea were given 500 mg portions of MSM together with 1,000 mg of ascorbic acid daily in fruit juice. All subjects with abnormal colon function returned to normal and remained normal while MSM was included in their diet. An additional seven patients with colon stasis were given 500 mg/day orally MSM alone and normalcy was provided by about the third day of MSM ingestion. One subject (M.M., M 22), partially paralyzed and bedridden for several years following a motorcycle accident had required both laxatives and enemas for bowel clearance. As with the ambulatory patients in this group, he returned to normal bowel function after beginning the MSM supplement as given in his breakfast fluids, and while slower in response, was normal within a week and thereafter did not require either chemical or physical bowel stimuli.

EXAMPLE VI

Epigastric Pain

A subject (A.B., F 56) with scleroderma who had used a variety of over-the-counter proprietary antiacid products for epigastric pain with limited benefit, was next evaluated with Tagamet ®. She obtained inadequate, short-term relief with dizziness as a side effect. Within a few days of ingesting ¼ tsp. of MSM twice daily, all epigastric discomfort stopped and relief has continued.

EXAMPLE VII

Inflammation of the Mucous Membranes Associated With Parasitical Infection

Parasites which injure the host present numerous serious problems for man and lower animals. On discovering that MSM has highly variable toxicities for various nematodes, tests were conducted on several parasites adverse to the health of vertebrates. *Trichomonas vaginalis*—ATCC Strain N#30001, was cultured in vitro employing diamonds TYM medium. MSM was added at levels from 5.5 to 109.3 mg/ml. A level of 5.5 to 10.9 mg/ml had no effect on this protozoan, while 21.9 mg/ml was inhibitory. All higher concentrations were lethal to this parasite. Based on this assay, MSM was roughly one-half as active as metronidazole HCl.

MSM was evaluated in vivo in conjunction with metronidazole HCl given to two subjects (S.R., F 25; H.L., F 31) 250 mg, taken every eight hours for ten days. Both had prior courses of therapy for this disorder without adequate response. MSM capsules of 500 mg size were administered orally with each Flagyl ® dose during the treatment period. During this course of treatment with concurrent MSM neither patient experienced stomach upset and nausea. This was a side-effect experienced by one subject during the first course of metronidazole HCl.

The concurrent treatment of MSM and Flagly ® was successful with both cases as evidenced by elimination of vaginal inflammation as confirmed by wet film examination. Stomach upset and nausea was not manifested. One subject was later reinfected by her sexual partner. This reinfection was cleared employing a daily douch of 5% aqueous MSM for one week. The subject's partner was successfully treated with 500 mg of MSM given twice daily for two weeks. Based on the body weight of each subject, a minimum systemic loading of MSM of 10 ppm was achieved.

EXAMPLE VIII

Mucuous Membrane Inflammation

Seven subjects with respiratory deficiency were given MSM orally in amounts ranging from 250-1,500 mg/day in single or divided units. Five presented emphysemic symptoms believed associated with cigarette smoking. Two presented tumor involvement of the lung with additional function impairment due to pleural fluid accumulation.

Two (A.F., F 69; H.Mc., M 67) of five subjects with emphysemic symptoms had prior cardiorespiratory function tests and follow-up evaluations at six and eight weeks after starting a course of 500 mg/day of MSM. Though both demonstrated several abnormal values prior to using MSM, particularly lowered aterial oxygen tension, both provided values in the normal range while ingesting MSM as a food supplement where the amount ingested provided blood levels above 5 ppm. MSM is readily assimilated systemically from the gut.

A more striking improvement was seen in physical achievement values determined with all subjects. Prior to and during the subject's ingestion of MSM, at approximately two-week intervals, all presenting emphysemic symptoms were required to walk a measured distance compatible with their physical resources. Within 2-4 weeks of first taking MSM, alone or with 1,000 mg of ascorbic acid/day, all subjects had at least doubled their "comfortable" walking distance. Two subjects (H.B. M 48; L.C., F 71) with lung tumors were evaluated by attending physicians and nurses as well as family as being more alert, comfortable, and with a better outlook and attitude. The lung cavity fluid problem of each subject disappeared during the first months taking of MSM. Both subjects were on radiation/chemotherapy which prior to MSM therapy had not produced an apparent benefit. However, significant regression of the tumor mass was observed in each case about one month after the subjects started a daily ingestion of MSM.

ALLERGIES

EXAMPLE IX

Environmental Allergies

Over 60 human subjects with allergy problems have reported amelioration of their allergy symptoms after successive daily doses of MSM varying from subject to subject from 50 to 1,000 mg/day. Their allergy symptoms varied from respiratory congestion to inflammation, itching, mucoid discharges and general discomfort.

This relief from the allergy symptoms did not mean that in all cases the anti-allergy medication the subjects had been taking could be eliminated, since MSM alone is not necessarily effective in totally eliminating physiological response to allergens. However, subjects with a chronic severe allergy problem have reported substantial to complete relief after the daily ingestion of MSM for several days, a week or, in some instances, a somewhat longer period. The majority of the subjects reported a significant reduction in concurrent anti-allergy medication required to maintain their allergy symptoms at the lowest achievable level. Subjects with allergic asthma or seasonal hay favor typically report equivalent or better control of symptoms with one-quarter or less the prior required level of medication. This reduction in rate of medication is significant in view of the side-effects usually associated with all anti-allergy medication.

The following specific examples illustrate the response of allergy sensitive individuals to diet supplemented MSM.

A subject (J.R., M 31) had exhibited striking and diverse allergic reactions to foreign substances since age 9. He was penicillin sensitive, reacted with a generalized rash to plasticizer or other additives in vinyl plastic upholstery and to many forms of pollen. He demonstrated a year around sensitivity to house dust. His case was reviewed by a number of allergy specialists and evaluated with various drugs and desensitizing courses without remarkable success. Initially, ¼ tsp./day MSM was included in his food or beverage when the spring pollen count was increasing and troublesome. He was not at the time on other medication and presented typical allergy symptoms including eye and nasopharygeal irritation, nasal discharge, sneezing and hoarsness. During the first week on MSM, a day-by-day improvement was noted in his condition. In the second week, he ingested ¼ tsp. of MSM, morning and night, and was symptom-free by the end of the second week. Since then he has included MSM in his daily diet, ajusting the intake to between ⅛-½ tsp. (roughly 250-1,000 mg) daily, with control of allergy dependent on allergen challenge.

Another subject (K.N., M 61) has been seen by allergists since his early twenties. This individual has been moderately benefitted by antihistamines and also by courses of desensitizing serums, although when given in the dilution increment courses he never tolerated the stronger serums, generally because of a systemic reaction. He was started on a course of MSM of ¼ tsp. per day in fruit juice and within 3 days reported a substantial improvement. He was at the time receiving antiallergy desensitization serum of ½ full strength, which caused a wheal and flare with persistent itching about the injection sites. After including MSM in the diet, the skin reaction subsided and for the first time after decades of attempted therapy, he tolerated full concentration desensitizing serum without systemic or local reaction. After 7 months including MSM in his diet, he reports being essentially free of allergy signs and symptoms.

Another subject (C.K., F 29) with pronounced pollen allergy had been on a proprietary "hay fever" drug in tablet tradenamed A.R.M. ® (chlorpheniramine maleate and phenylpropanolamine HCL) and a prescriptive nasal spray (Nasalide ®). In attempting to control the allergy, the subject had exceeded the recommended dosages with resultant undesirable side effects. Upon ingesting ¼ tsp. of MSM night and morning, by day three she was in better control of her allergy, even though the spray was discontinued and the A.R.M ® dosage was dropped to ½ tsp. once each day at nighttime (1/12th her previous daily intake). After four months on MSM therapy, she is symptom-free but continues the MSM and ½ tablet of A.R.M ®.

EXAMPLE X

Food and Drug Allergies

Subjects who manifest an allergic response to drugs, e.g., aspirin and Indocin ®, and who are mildly to severely allergic to various foods, e.g., cereals, shrimp, and other seafood, milk, etc., report a lessened intolerance or complete tolerance thereto when 100–1,000 mg of MSM is ingested therewith. Thus, a major application for MSM as a prophalactic safeguard against allergic response to orally ingested drugs and foods or beverages that are allergens or irritants to subjects sensitive thereto, is by ingesting MSM concurrently or in admisture therewith.

EXAMPLE XI

Insect Bites

Subjects ingesting daily amounts of MSM sufficient to raise their blood levels above 1 ppm, manifest much milder than usual wheal and flare or pruritis following insect bites and usually more rapid subsidence. All subjects reported a significant reduction in post-bite irritation and itching.

Interestingly, subjects ingesting about 500 mg of MSM daily as a dietary supplement exhibit lessened attraction to mosquitos, particularly those who also are supplementing their diet with Vitamin B complex and during period of perspiration, when mosquitos are usually more attracted.

EXAMPLE XII

Hypertension Associated With Stress

Three male subjects (R.G., M 65; J.W., M 47; R.H., M) on regulated diets and managed with conservative medication for uncomplicated hypertension had diastolic blood pressure consistently above 90 mm Hg. After receiving 500 mg/day of MSM orally, the blood pressure (systolic and diastolic) of each subject lowered within 4–6 weeks to normal parameters.

EXAMPLE XIII

Free Flowing Powder

A solution of one gram of 2-(4-thiazolyl)benzimidazole, a broad spectrum anthelmintic and fungicide, in nine grams of molten MSM, when allowed to cool to ambient temperature can be readily reduced to a flowable powder, which can be recompressed into tablets or used to fill capsules. The solid solution readily disperses in water or gastric solution at 37° C. and hence is almost instantly available for gut absorption following ingestion. MSM is generally compatible with most dosage form excipients, (two exceptions are mineral oils and paraffin waxes but waxes of vegetable orgin are generally compatible).

Compositions with Improved Flow Properties

Although pulverized and microcrystalline forms of dry MSM have good flow properties, their flow properties are significantly improved by the presence therein of from about 0.25–2% by weight of fumed or colloidal silica, particularly where traces of moisture remain in the MSM.

EXAMPLE XIV

Timed Release Tablets

A tablet formed from 250 mg of MSM, 250 mg of vitamin C, 25 mg of potassium bicarbonate, 20 mg of glycine, and 10 mg of magnesium stearate will totally disintegrate in simulated gastric fluid after less than 15 minutes. By adding various state of the art tableting and granulation excipients, e.g., C-10 to C18 fatty acids and fatty alcohols, polyvinyl alcohol, rosin, dl-pantothenyl alcohol, cellulose esters and ethers, polyvinyl acetate, starches, beeswax and calcium carbonate, it is possible to regulate disintegration over a period of at least ten hours.

A tablet formed from 200 mg of MSM, 200 mg of vitamin C, 10 mg glycine, 10 mg magnesium stearate, 5 mg polyvinyl acetate, 5 mg hydroxypropyl methyl cellulose, 10 mg stearic acid and 10 mg of cetyl alcohol uniformly disintegrated in simulated gastric fluid over a five hour period after which period total disintegration was observed.

A table containing 100 mg of MSM, 25 mg potassium penicillin G (or other active agents must be protected from gastric acids), 10 mg glycine, 10 mg calcium stearate, 30 mg starch, 15 mg cetyl alcohol and 15 mg of hydrogenated rosin released 65% of the K penicillin G by hour 6 and 95% by hour 10. In this preparation, a melt of the MSM and hydrogenated rosin was solidified to form a solid solution and micronized prior to blending with the other ingredients. By controlling the release rate of the unit dosage form, the active agent can pass safely through the stomach and into the more favorable environment for adsorption of the small intestine.

The effect of MSM on bioavailability of a pharmaceutical compound, viz., aspirin, was determined using commercial 5 grain aspirin tablets (Bayer ®) and tablets formed from 5 grains (0.324 grams) of calcium acetylsalicylate, 0.0314 grams potassium bicarbonate, 0.0026 grams magnesium stearate and 0.290 grams MSM (milled powder containing 2% by weight of a food and drug grade colloidal silica). Four tablets of either the commercial or test aspirin product were combined in ground meat and fed to 12-hour starved mongrel dogs. Blood was drawn from each dog at 5 minute intervals during the first 0.5 hour and at 15 minute intervals thereafter. The peak blood level with the commercial aspirin occurred at 20 minutes, while the peak level with the test tablets was at 15 minutes. The commercial aspirin could not be detected in the 2.5 hour blood samples, whereas the test tablets provided an analyzable concentration of aspirin in the blood at 3.0 hours post administration.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

I claim:

1. A pharmaceutical composition adapted for oral ingestion comprising a mixture of (a) gastrointestinal upset-promoting but otherwise physiologically acceptable pharmaceutically-active agent selected from the group consisting of analgesics, anti-neoplastic agents, anti-inflammatory agents, cardiovascular agents, antibiotics and other chemotherapeutants for microbial diseases, and (b) a gastrointestinal upset-ameliorating effective amount from about 100 to 1,000 mg of methylsulfonymethane.

2. A composition according to claim 1, in the form of tablets, capsules, dragees or pills.

3. A composition according to claim 1, wherein the composition contains from about 250 to 500 mg of methylsulfonymethane per unit dosage.

4. A composition according to claim 1, wherein the pharmaceutically-active agent is an analgesic.

5. A composition according to claim 1, wherein the pharmaceutically-active agent is an aspirin.

6. A flowable powder adapted for compression into orally ingestible tablets, wherein the powder particles consist essentially of a pharmaceutically orally active agent selected from the group consisting of analgesics, anti-neoplastic agents, anti-inflammatory agents, cardiovascular agents, antibiotics and other chemotherapeutants for microbial diseases, suspended or dissolved in an amount from about 100 to 1,000 mg of methylsulfonylmethane effective to improve the flow characteristics of the former in powder form.

7. The flowable powder according to claim 6 wherein the pharmaceutically-active compound is dissolved in the methylsulfonylmethane.

8. The flowable powder according to claim 6 wherein the powder particles are substantially anhydrous and the pharmaceutically-active agent is unstable in the presence of moisture.

9. A pharmaceutical composition in granule or tablet form adapted for oral ingestion and comprising a pharmaceutically orally-active agent selected from the group consisting of analgesics, anti-neoplastic agents, anti-inflammatory agents, cardiovascular agents, antibiotics and other chemotherapeutants for microbial diseases, and a granulating or tableting adjuvant, respectively, consisiting predominantly of from 100 to 1,000 mg of methylsulfonylmethane.

10. The pharmaceutical composition according to claim 9 in tablet form.

11. The pharmaceutical composition according to claim 9 in granule form and contains from 0.25 to 2% colloidal silica.

* * * * *